(12) United States Patent
Doya

(10) Patent No.: US 10,434,486 B2
(45) Date of Patent: Oct. 8, 2019

(54) DEVICE FOR PRODUCING PARTICLES AND METHOD FOR PRODUCING PARTICLES

(71) Applicant: TSUKISHIMA KIKAI CO., LTD., Tokyo (JP)

(72) Inventor: Yo Doya, Tokyo (JP)

(73) Assignee: Tsukishima Kikai Co., Ltd., Tokyo (JP)

( * ) Notice: Subject to any disclaimer, the term of this patent is extended or adjusted under 35 U.S.C. 154(b) by 0 days.

(21) Appl. No.: 16/072,052

(22) PCT Filed: Jan. 11, 2017

(86) PCT No.: PCT/JP2017/000531
§ 371 (c)(1),
(2) Date: Jul. 23, 2018

(87) PCT Pub. No.: WO2017/130687
PCT Pub. Date: Aug. 3, 2017

(65) Prior Publication Data
US 2019/0022551 A1   Jan. 24, 2019

(30) Foreign Application Priority Data

Jan. 27, 2016   (JP) .................................. 2016-013593

(51) Int. Cl.
*B01J 19/00* (2006.01)
*B01D 9/00* (2006.01)
(Continued)

(52) U.S. Cl.
CPC .......... *B01J 19/0066* (2013.01); *B01D 9/005* (2013.01); *B01D 9/02* (2013.01); *B01F 3/08* (2013.01);
(Continued)

(58) Field of Classification Search
CPC ................ B01J 19/0066; B01J 19/1837; B01J 19/1881; B01J 14/00; B01J 10/00;
(Continued)

(56) References Cited

U.S. PATENT DOCUMENTS 2,467,470 A   4/1949 Gerhold et al.
3,015,128 A   1/1962 Somerville
(Continued)

FOREIGN PATENT DOCUMENTS

EP   0060603   9/1982
GB   1507722   4/1978
(Continued)

OTHER PUBLICATIONS

International Search Report and Written Opinion, PCT/JP2017/000531, dated Mar. 14, 2017.
European Search Report for EP 17743918.9, dated Aug. 1, 2019.

*Primary Examiner* — Lessanework Seifu
(74) *Attorney, Agent, or Firm* — Andrus Intellectual Property Law, LLP

(57) ABSTRACT

A method of producing particles by bringing plural dissimilar materials A and B into contact with each other includes feeding a liquid into a reactor from a first end portion of the reactor such that the liquid flows along the inner peripheral surface of the reactor and generating a vortex flow toward a second end portion in the reactor by the feed of the liquid; disposing a flow-assisting blade capable of rotating around the central axis line in the reactor and rotating the flow-assisting blade; and injecting materials to be contacted A and B into the reactor, discharging a contacted liquid from the second end portion of the reactor, and generating the particles in the contacted liquid.

10 Claims, 28 Drawing Sheets

(51) Int. Cl.

| | | |
|---|---|---|
| *B01D 9/02* | (2006.01) | |
| *B01F 5/10* | (2006.01) | |
| *B01F 7/16* | (2006.01) | |
| *B01F 7/26* | (2006.01) | |
| *B01J 14/00* | (2006.01) | |
| *B01F 3/08* | (2006.01) | |
| *C01F 7/34* | (2006.01) | |
| *C01F 11/18* | (2006.01) | |
| *C01G 9/02* | (2006.01) | |
| *C07C 227/42* | (2006.01) | |
| *C07C 229/08* | (2006.01) | |
| *B01F 5/00* | (2006.01) | |
| *B01J 10/00* | (2006.01) | |
| *B01J 19/18* | (2006.01) | |

(52) U.S. Cl.
CPC .............. *B01F 5/0065* (2013.01); *B01F 5/10* (2013.01); *B01F 7/16* (2013.01); *B01F 7/26* (2013.01); *B01J 10/00* (2013.01); *B01J 14/00* (2013.01); *B01J 19/00* (2013.01); *B01J 19/1837* (2013.01); *C01F 7/34* (2013.01); *C01F 11/18* (2013.01); *C01G 9/02* (2013.01); *C07C 227/42* (2013.01); *C07C 229/08* (2013.01); *B01D 2009/0086* (2013.01); *B01F 2005/004* (2013.01); *B01F 2005/0017* (2013.01); *B01J 2204/002* (2013.01); *B01J 2219/00166* (2013.01); *B01J 2219/185* (2013.01); *B01J 2219/1943* (2013.01)

(58) Field of Classification Search
CPC ..... B01J 19/00; B01J 2204/002; B01D 9/005; B01D 9/02; B01F 5/0065; B01F 7/16; B01F 7/26; B01F 5/10; B01F 3/08; B01F 2005/004; B01F 2005/0017; C07C 229/00; C07C 227/42; C01G 9/02; C01F 11/18; C01F 7/34
See application file for complete search history.

(56) References Cited

U.S. PATENT DOCUMENTS

| | | | |
|---|---|---|---|
| 3,502,305 A | 3/1970 | Grun | |
| 4,116,163 A | 9/1978 | Torelli et al. | |
| 4,444,510 A | 4/1984 | Janssen | |
| 6,467,947 B1* | 10/2002 | Welsh | ................... B01F 3/0853 366/279 |
| 2005/0093211 A1 | 5/2005 | Shiraishi et al. | |
| 2011/0177243 A1 | 7/2011 | Houben et al. | |
| 2013/0045421 A1 | 2/2013 | Kobino et al. | |
| 2014/0003189 A1 | 1/2014 | Gerl et al. | |
| 2015/0188133 A1 | 7/2015 | Doya et al. | |

FOREIGN PATENT DOCUMENTS

| | | |
|---|---|---|
| JP | 62-270406 | 11/1987 |
| JP | 2004-043451 A | 2/2004 |
| JP | 2005-133135 | 5/2005 |
| JP | 58-8541 | 5/2010 |
| JP | 2011105588 | 6/2011 |
| JP | 5466732 | 4/2014 |
| JP | 2014-511755 | 5/2014 |
| WO | 2012/123441 | 9/2012 |
| WO | 2013190861 | 12/2013 |

* cited by examiner

Fig. 4 (a)
Fig. 4 (b)
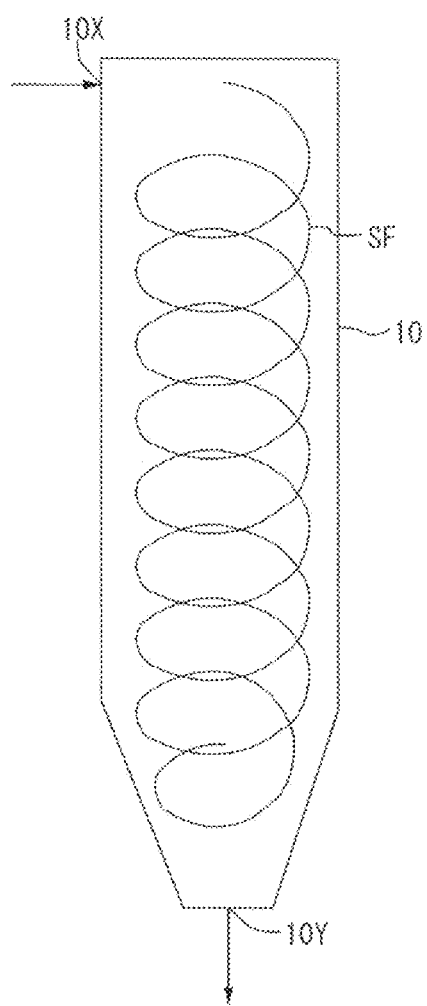
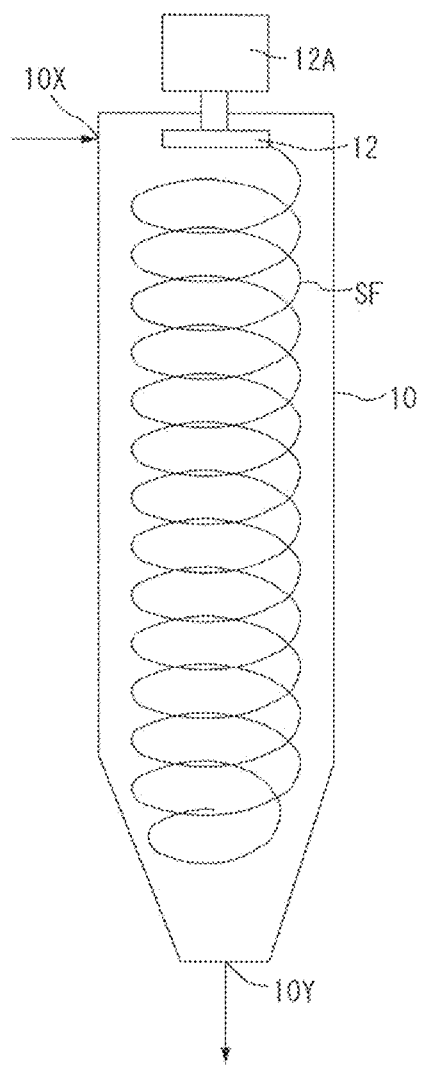

DEVICE FOR PRODUCING PARTICLES AND METHOD FOR PRODUCING PARTICLES

CROSS-REFERENCE TO RELATED APPLICATIONS

This application is the U.S. national stage application of International Application PCT/JP2017/000531, filed Jan. 11, 2017, which international application was published on Aug. 3, 2017, as International Publication WO 2017/130687 in the Japanese language. The International Application claims priority of Japanese Patent Application No. 2016-013593, filed Jan. 27, 2016. The international application and Japanese application are both incorporated herein by reference, in entirety.

TECHNICAL FIELD

The present invention relates to a device for producing particles and a method of producing particles.

BACKGROUND ART

The industrial fields of cosmetics, catalysts, electronic materials, battery materials, fine ceramics, pharmaceuticals, and foods involve production of particles, in particular, fine particles.

In general, two or more reactants are fed in a stirred reactor equipped with a stirrer, the reactants are mixed in a liquid to prepare the liquid containing a reaction product (produced particles), and the reaction product (produced particles) is separated from the liquid. A typical example of this process is disclosed in Patent Literature 1.

Unfortunately, in the production of particles in this stirred reactor, the diffusion of the solution of the reactants is the rate-determining factor, causing local reaction to readily give crystals irregular in size and shape. In addition, preparation of fine particles needs to increase the rotation speed of the stirring blade, which requires high power and is not economical.

Patent Literature 2 discloses an apparatus for producing sodium hypochlorite. This apparatus generates a spiral flow in a cylindrical shaped vertical reactor by inflow of a circulating reaction liquid into the vertical reactor in the tangential direction, and chlorine gas is fed from below the spiral flow to be brought into contact with an aqueous sodium hydroxide liquid.

Although the reactor of Patent Literature 2 has an advantage of a high contact efficiency of the chlorine gas by virtue of the spiral flow, the contact efficiency to the target only by the spiral flow is not sufficient.

Further, the present inventors have proposed a crystallizer that can produce crystals improved in uniformity of the size and shape as shown in Patent Literature 3 and have verified the advantages. However, the inventors have found that this crystallizer exhibited a limited improvement because it used only a spiral flow.

CITATION LIST

Patent Literature

[Patent Literature 1] Japanese Unexamined Patent Application Publication No. 2011-105588
Patent Literature 2] Japanese Unexamined Patent Application Publication No. 62-270406
[Patent Literature 3] Japanese Patent No. 5466732

SUMMARY OF INVENTION

Technical Problem

Accordingly, a first object of the present invention is to provide particles having uniform sizes and shapes. A second object of the present invention is to reduce the power cost in producing the particles. Other objects will become apparent from the following description.

Solution to Problem

The present invention relates to a method of producing particles by bringing plural dissimilar materials into contact with each other and a device therefor.

In the present invention, a liquid is fed from one end (a first end) portion of a reactor having a volume and, for example, a circular-shaped or elliptical-shaped inner circumference such that the liquid flows along the inner peripheral surface of the reactor. This inflow of the liquid generates a vortex flow toward the other end (the second end) portion in the reactor.

According to the present invention, in the reactor, a flow-assisting blade for the liquid is provided to be rotatable around the central axis line, and the blade is rotated to increase the vortex flow velocity. Since the vortex flow is accelerated in this way, in the present invention, the blade is referred to as the "flow-assisting blade".

Materials to be treated are injected into the reactor. The contacted liquid is discharged from the second end portion of the reactor.

Injection of the materials to be contacted into the vortex flow generated in the reactor brings the materials to be contacted into contact with the vortex flow (high turbulent energy field) to generate particles by the contact.

Injection of the materials to be contacted into the vortex flow as a high turbulent energy field causes effective contact between dissimilar materials to certainly generate particles, in particular, fine particles.

For example, when the dissimilar materials react with each other by coming into contact with each other, injection of the reactants (materials to be contacted) into the reactor causes contact of the reactants with the vortex flow to start the reaction. Subsequently, the reactants are caught into the vortex flow to cause powerful mixing and diffusion, so that the reaction proceeds at a high speed.

In the present invention, the flow-assisting blade is rotated. Based on extensive studies involving various experiments, the mechanism generated by rotation of the flow-assisting blade according to the invention is presumed as follows:

The rotation of the blade increases the vortex flow velocity to accelerate the mixing and diffusion of materials. For example, when the reactants (materials to be treated) are added to the vortex flow in the contact reaction with the mixing and diffusion, the vortex flow velocity is increased by the rotation of the flow-assisting blade to further accelerate the mixing and diffusion. Pitches of the vortex flow with the high velocity of the reactants (materials to be treated) become fine until the materials reach the outlet of the reactor. In other words, the rotation distance in the vortex flow is elongated like a screw thread with a fine pitch.

Accordingly, the retention time of the reactants in the reactor is prolonged. In addition to the increase in the retention time of the reactants (materials to be treated), the vortex flow velocity is increased, thus the reactants (materials to be contacted) sufficiently react with the liquid of other kinds of materials to be contacted resulting in formation of microparticles at a high rate.

In such a mechanism according to the present invention, the resulting particles (e.g., crystal particles or agglomerated particles) can have uniform sizes and shapes and aggregation of particles is accelerated so that the agglomerated particles are further grown. The flow-assisting blade can be downsized. Further, the liquid is not stirred by the flow-assisting blade alone and the motive power for the rotation of the flow-assisting blade thus should be enough to rotate itself for assisting the vortex flow, hence, the power expense is not costly.

All or part of the contacted liquid discharged from the second end portion of the reactor may be fed into the reactor from the first end portion of the reactor such that the liquid flows along the inner peripheral surface of the reactor. In brief, this embodiment forms a circulation system (path). In such a case, all or part of the reaction liquid is recycled in the circulation system.

Particles are recovered by solid-liquid separation of the part of the contacted liquid taken out from the circulation system in which the contacted liquid discharged from the second end portion of the reactor is sent to the first end portion of the reactor.

The liquid (the contacted liquid in the case of a circulation system) is desirably fed, at an inflow velocity of 0.5 m/sec or more, into the reactor from the first end portion. Such an inflow velocity generates a strong vortex flow.

The materials to be contacted can be added in a direction from one side (a first side) to the other side (a second side). In such a case, the materials to be contacted may be injected from the outside of the reactor toward the central axis line. However, the injection of the reactants in the reverse direction, i.e., in the direction from the second side toward the first side, counters the flow and is unpreferable.

The device according to the present invention for producing particles by bringing plural dissimilar materials into contact with each other comprises:
  a reactor;
  a liquid inflow means including an inlet at a first end portion of the reactor such that a flow line from the inlet is directed along the inner peripheral surface of the reactor;
  a flow-assisting blade, which is disposed inside the reactor;
  a driving means for rotating the flow-assisting blade;
  an injection means for injecting materials to be contacted into the reactor; and
  an outflow means for discharging the contacted liquid from the second end portion of the reactor.

The device may include a circulation system for introducing all or part of the contacted liquid discharged by the outflow means to the inflow means.

The device can further include a solid-liquid separation means including an extraction path for extracting part of the contacted liquid from the circulation system and collecting produced particles by solid-liquid separation of the extracted liquid from the extraction path.

The flow-assisting blade may have a disk shape intersecting with the central axis line of the vortex flow.

The flow-assisting blade may have a disk shape provided with a concave-convex portion in the periphery thereof.

The flow-assisting blade may include a disk-shaped body intersecting with the central axis line of the vortex flow and a protrusion protruding to the second side at least in the periphery of the disk-shaped body and intersecting an assumed circle having the center on the central axis line.

Advantageous Effects of Invention

According to the present invention, the resulting particles can have uniform sizes and shapes. There is also an advantage that the particles can be produced at the low power cost.

Furthermore, particles having a small particle size and a sharp particle size distribution can be prepared. A large amount of reaction processing per unit time can be achieved with small facilities.

BRIEF DESCRIPTION OF DRAWINGS

FIG. 4 includes schematic diagrams (a) and (b) explaining generation of vortex flows.

DESCRIPTION OF EMBODIMENTS

The present invention provides a method and a device for producing particles, in particular, microparticles by bringing plural dissimilar materials into contact with each other in the industrial fields of cosmetics, catalysts, electronic materials, battery materials, fine ceramics, pharmaceuticals, and foods.

In the method of preparing microparticles of the present invention, the solubility of the materials in a solution is controlled. More specifically, the microparticles are generated by varying some parameters of the solution, such as concentration, temperature, pH, and redox potential while a supersaturation state of the dissolved materials is transformed to a stable or metastable state of the dissolved materials.

In order to generate uniform microparticles, it is significantly important to control the flow field in the reaction field to achieve a uniform supersaturation distribution in the reaction field.

In the present invention, plural dissimilar materials are brought into contact with each other. The invention includes the following embodiments:
(1) The supersaturation is controlled by bringing plural dissimilar materials into contact with each other (by causing the materials to react with each other in the case where the dissimilar materials are reactive);
(2) The supersaturation is controlled by addition of a poor solvent such as alcohol (referred as poor solvent process); and
(3) The supersaturation is controlled by injection of a cooling liquid or cooling gas.

In these embodiments, the number of materials to be contacted (reactants) is not limited.

The details of the present invention will now be described by a typical case that the plural dissimilar materials are two reactants (reactive materials) A and B reacting with each other.

Figure 1:
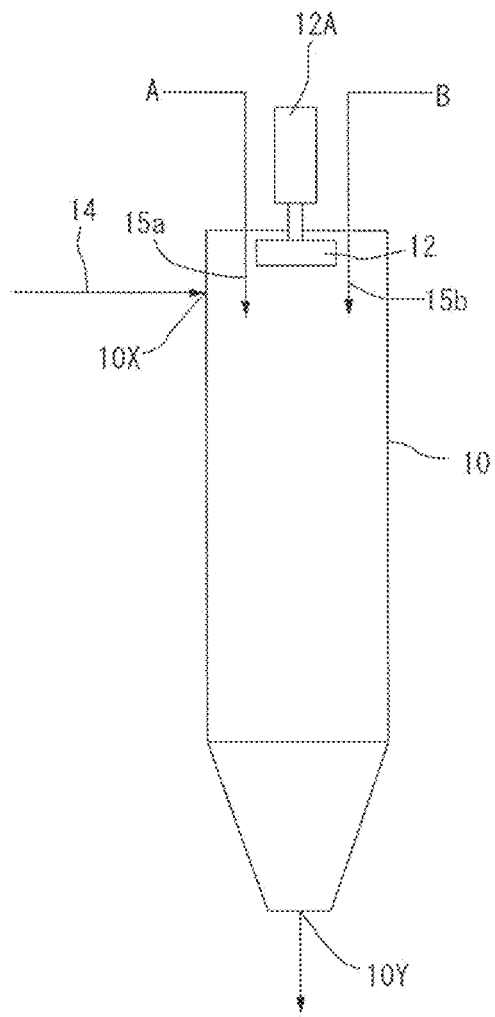
FIG. 1 a schematic diagram of a first example of the present invention.
Figure 2:
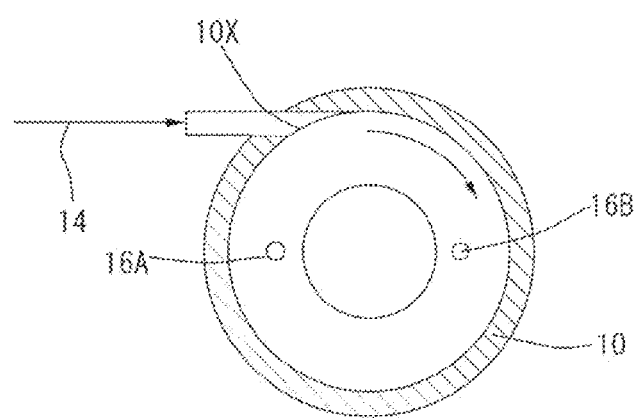
FIG. 2 is a lateral cross-sectional view of the example.

FIGS. 1 and 2 illustrate a first example of the present invention. The liquid flow in a reactor 10 is set to be a vortex flow, and an additional liquid containing reactants (reactive materials) to be added A and B is injected into the reaction field in the reactor 10 for performing contact processing (for performing reaction processing in this example), while a contacted liquid is discharged to the exterior of the system.

In the example illustrated in the drawings, as the additional liquid containing materials to be added, the additional liquid containing the materials A and B, a gas (an inert gas such as a nitrogen gas or a carbon dioxide gas, or an active gas such as hydrogen or ammonia) may be injected together in parallel with the materials A and B.

In the first example, the additional liquid is injected toward the reaction field of the additional liquid in the downstream direction of the vortex flow of the liquid.

Although the reactor 10 illustrated in the drawings is vertically installed, the reactor 10 may be horizontally installed since there is no effect on the vortex flow in principle by the install direction of the reactor 10.

The depicted reactor 10 has a cylindrical shape (with a circular-shaped inner circumference). Although a vortex flow can be generated even when the reactor 10 has an elliptical-shaped or polygonal-shaped inner circumference, the inner circumference is desirably circular-shaped or polygonal-shaped with many sides, at least five sides, to generate smoothly the vortex flow. Since it is necessary for the vortex flow just to be generated inside the reactor 10, as for the outer shape of the reactor 10, there is no limitation.

A liquid 14 is fed into the reactor 10 from an inlet 10X disposed at a first end portion (the upper end portion in the drawings). The liquid 14 may be a fresh liquid to be added (the reactants may be contained or may not be contained in the fresh liquid) or a returned liquid sent back in a circulation system as the reaction liquid (contacted liquid) after the reaction between the materials A and B, as described in an example below.

In order to generate a vortex flow by feeding the liquid 14 into the reactor 10 from the inlet 10X, it is desirable to feed the liquid 14 substantially along the tangential direction to the inner peripheral surface as shown in FIG. 2.

In the present invention, a flow-assisting blade 12 rotatable around the central axis line is disposed in the reactor 10, and the flow-assisting blade 12 is rotated with a rotary driving means, for example, a motor 12A. The vortex flow velocity is increased by the rotation of the flow-assisting blade 12.

The reactants (additional liquid containing materials A and B) are injected into the reactor 10. In such a case, injection nozzles 15a and 15b are desirably disposed outboard from the flow-assisting blade 12 in planar view (in the case where the injection nozzles 15a and 15b are inboard from the flow-assisting blade 12, for example, the flow-assisting blade 12 is divided into a fixed central portion and a rotating outer portion and the injection nozzles 15a and 15b extend through the central portion).

The open ends of the injection nozzles 15a and 15b may be above the under surface of the flow-assisting blade 12 or may be below the under surface.

The open ends of the injection nozzles 15a and 15b are desirably disposed in the vortex flow.

The reaction liquid is discharged from an outlet 10Y of the second end portion of the reactor 10 (the lower end portion in the drawings).

Figure 3:
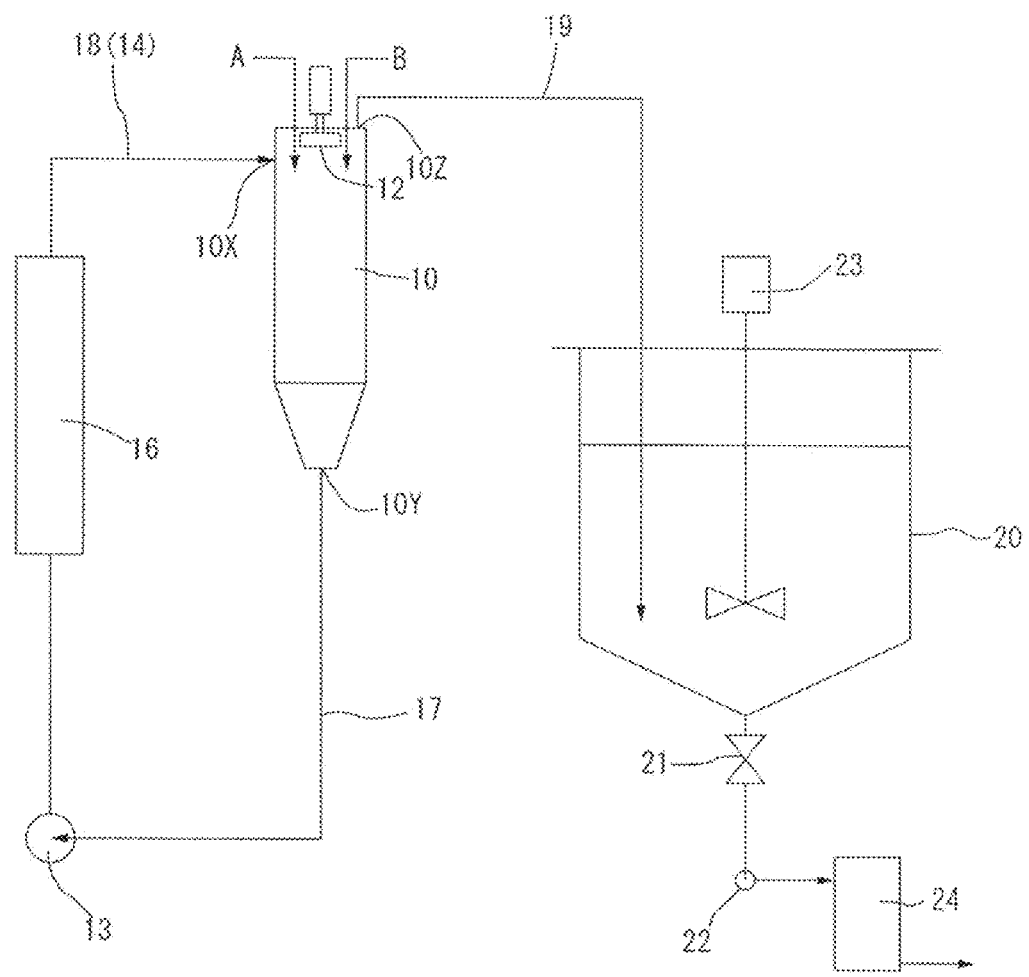
FIG. 3 is a schematic diagram of a second example.

FIG. 3 illustrates a second example wherein a circulation system is formed. In detail, the reaction liquid is discharged from the outlet 10Y at the lower end portion of the reactor 10 and is circulated with a circulation pump 13 through circulation paths 17 and 18, and the contacted liquid is fed into the reactor 10 to generate a vortex flow. A regulator 16, which is for cooling, heating or the like of the liquid, may be provided if required.

In the circulation system, the contacted liquid may be transferred from the midway of the circulation path 17 or the circulation path 18 to a subsequent facility or may be transferred from an overflow port 10Z of the reactor 10 to the subsequent facility as shown in the second example of FIG. 3.

In the second example of FIG. 3, the final (reaction) contacted liquid is discharged from the overflow port 10Z and is introduced to a storage vessel 20 through an extraction path 19. At appropriate timing, an extraction valve 21 is opened to introduce a particle liquid to a final production step, for example, a solid-liquid separation step 24 with an extraction pump 22. A stirrer 23 may be disposed inside the storage vessel 20.

In the process described above, a liquid is fed from the inlet 10X in the first end portion of the reactor 10 such that the liquid flows along the inner peripheral surface of the reactor 10. Since the liquid is fed in this way, the vortex flow is generated which directs toward the second end portion within the reactor 10.

In the present invention, as shown in FIG. 1, a flow-assisting blade 12 rotatable around the central axis line is disposed in the reactor 10, and the vortex flow velocity is increased by such rotation of the flow-assisting blade 12.

This will be schematically described. As shown in FIG. 4(a), in the case that any flow-assisting blade 12 is not provided, the pitches of the vortex flow SF are rough. In contrast, as shown in FIG. 4(b), in the case that a flow-assisting blade 12 is provided according to the present invention, the pitches of the vortex flow SF are fine. This indicates that the flow-assisting blade 12 can increase the energy of the vortex flow.

FIG. 4 is merely conceptual. Since an actual liquid flow is continuous in the vertical direction, "pitches of the vortex flow" are not actually present. FIG. 4 conceptually illustrates, for example, the trace of the movement flow of a material added to the vortex flow.

Figure 5:
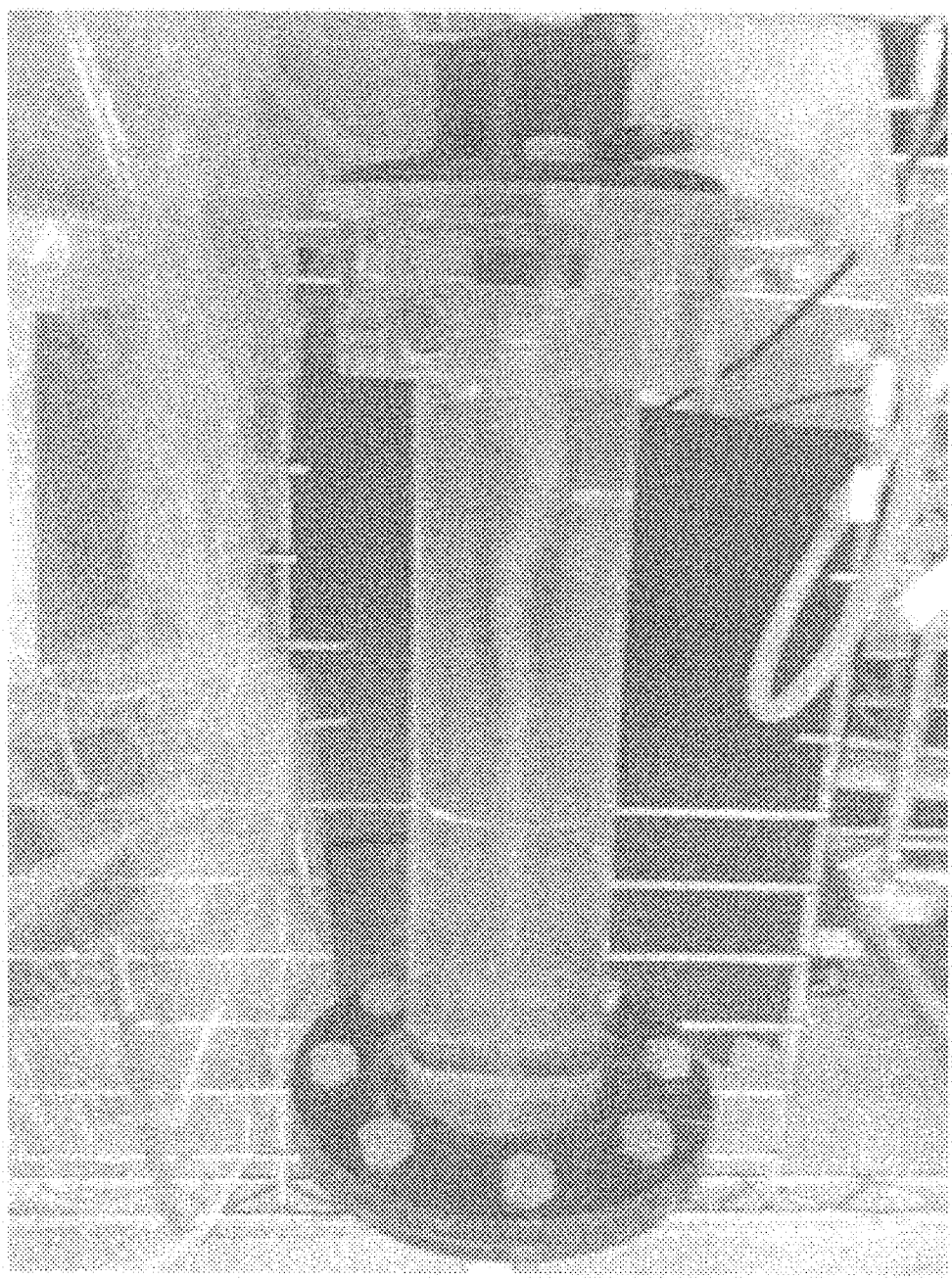
FIG. 5 is an explanatory photograph of a device not including a flow-assisting blade.
Figure 6:
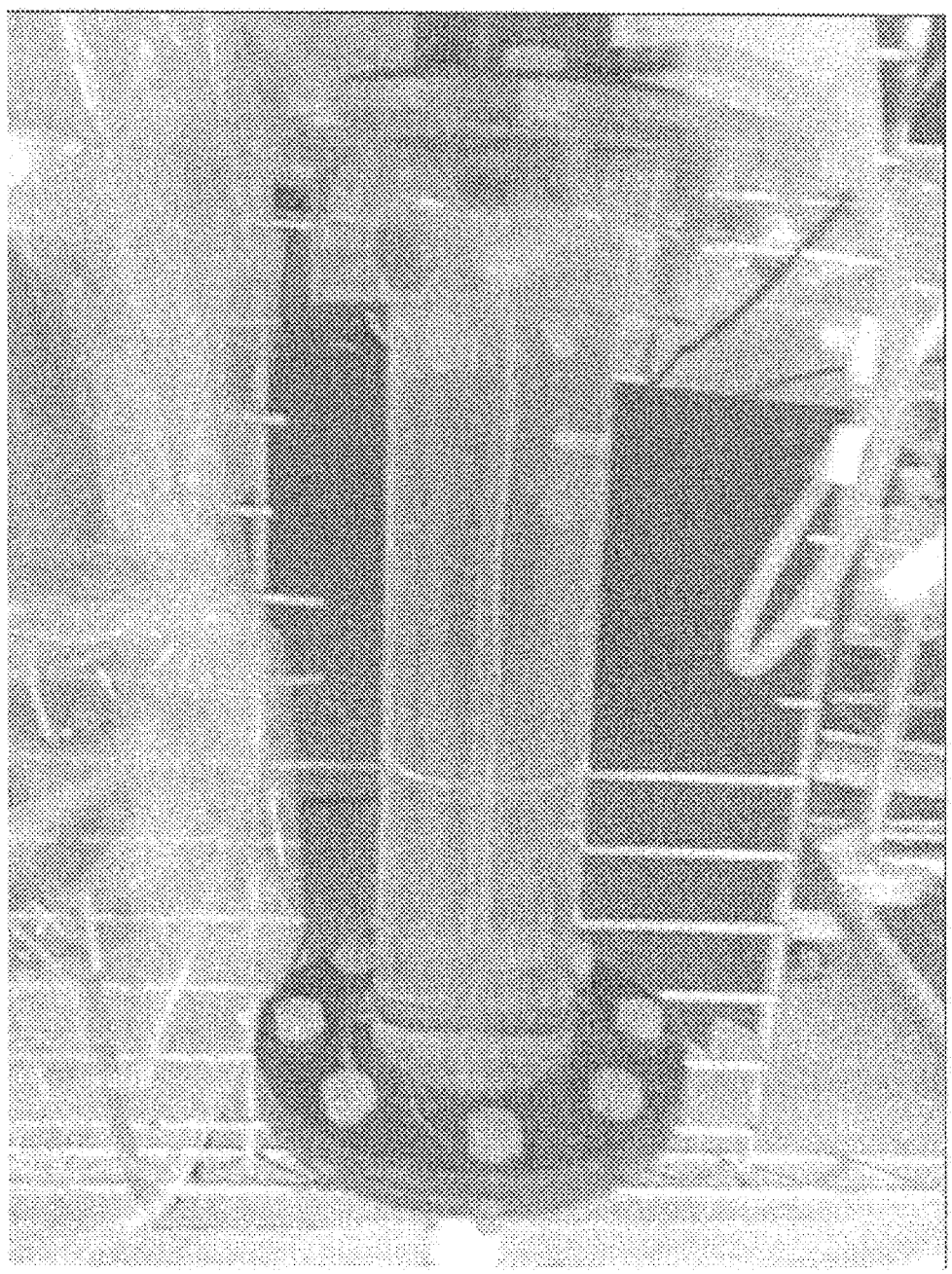
FIG. 6 is an explanatory photograph of a device including a flow-assisting blade.

An experiment for verifying this conception was carried out. The following two states of the vortex flow were visually observed. In the first state, a liquid is fed from an inlet at the upper end portion of a cylindrical shaped reactor such that the liquid flows along the inner peripheral surface of the reactor as shown in FIG. 5. In the second case, a reactor is provided with a flow-assisting blade as shown in FIG. 6. In both cases, air was injected from the top into each reactor for clarification of visual verification.

Close observation of FIG. 5 reveals that a high-speed flow field (the whitened portion) around the central axis of the reactor due to the vortex flow has a slightly larger diameter and that the flow has a fluctuation in the upper portion. In contrast, close observation of FIG. 6 including the flow-assisting blade reveals that a high-speed flow field (the whitened portion) around the central axis of the reactor has a smaller diameter and that the flow is approximately straight from the lower portion to the upper portion. The comparison of FIG. 5 with FIG. 6 also demonstrates the fact described above.

The reactants A and B are injected into the reactor 10 under the large energy of the vortex flow. The reaction liquid is discharged from the outlet 10Y on the second end portion of the reactor 10.

The reactants are injected into the vortex flow SF generated in the reactor 10 and are brought into contact with the vortex flow to cause powerful diffusion and mixing (contact), progress of a reaction, and generation of microparticles.

Based on extensive studies involving various experiments, the mechanism generated by rotation of the flow-assisting blade according to the invention is presumed as follows:

Materials to be contacted (e.g., reactants) injected into the reactor are brought into contact with a vortex flow having the large energy to start diffusion and mixing. Subsequently, the materials to be contacted (e.g., reactants) are caught into the vortex flow to cause powerful mixing and diffusion, resulting in a high-speed reaction.

Since the vortex flow velocity is increased, the pitches of the vortex flow of the reactants are shorten until the materials reach the outlet of the reactor. In other words, the rotation distance in the vortex flow is elongated like a screw thread with a fine pitch.

Accordingly, the reactants have a prolonged retention time in the reactor. In addition to the prolonged retention time of the reactants, the vortex flow velocity is increased, thus the materials to be contacted (e.g., reactants) sufficiently react with the liquid (e.g., contacted liquid), resulting in formation of microparticles at a high rate.

In such a mechanism according to the present invention, the resulting particles (e.g., precipitated particles, crystal particles, or agglomerated particles) can have uniform sizes and shapes. Alternatively, aggregation of particles is accelerated to grow agglomerated particles.

The flow-assisting blade can be downsized. Further, the liquid is not stirred by the flow-assisting blade alone and the motive power for the rotation of the flow-assisting blade thus should be enough to rotate itself for assisting the vortex flow, hence, the power expense is not costly.

The reactants may be injected from any position closer to the center of the reactor 10 than the inner wall surface in the reaction field in the reactor 10, and the injection position is preferably located within ⅔ of the radius r as the distance in the radial direction from the center.

When the reactants are injected from the top as shown in FIG. 1, the injection position may be on the slightly outer side in relation to the position of the flow-assisting blade 12.

Figure 7:
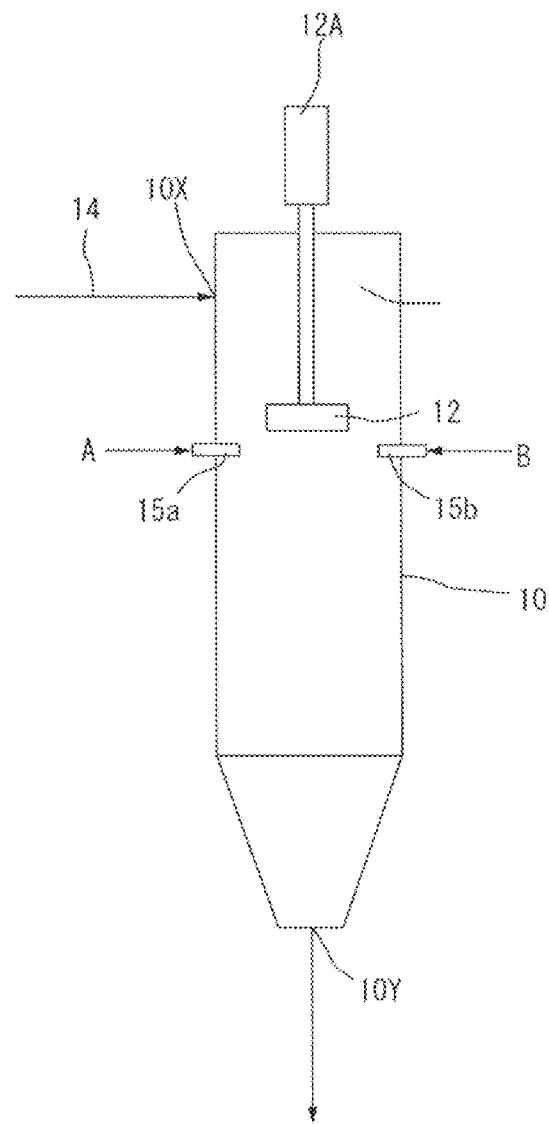
FIG. 7 is a schematic diagram of another example of the present invention.
Figure 8:
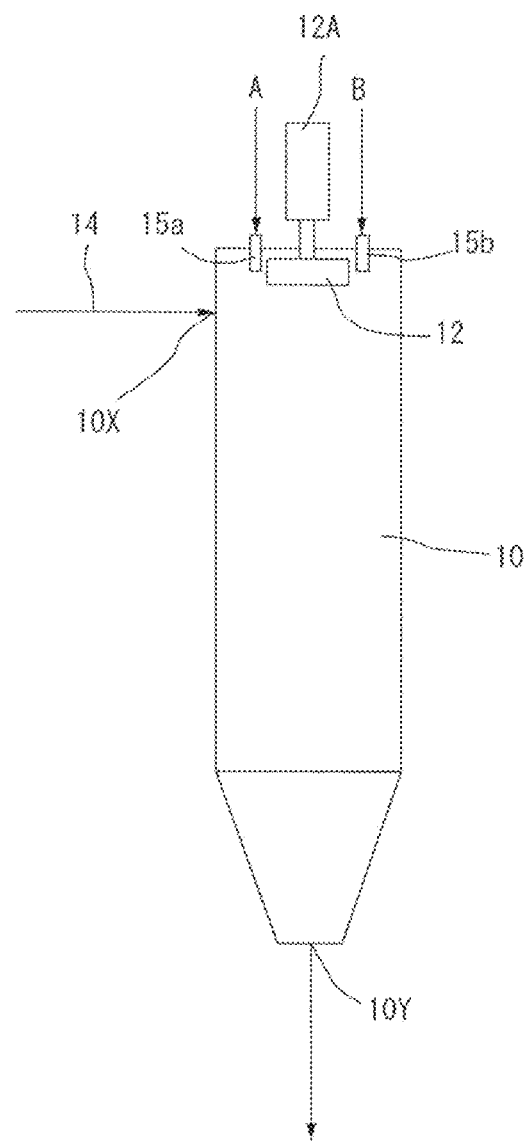
FIG. 8 is a schematic diagram of another example of the present invention.

As shown in FIG. 7, the reactants may be injected into the reactor 10 through the side wall from the exterior. The position of the flow-assisting blade 12 in the height direction may be lower than the inlet 10X, as shown in FIG. 7. As shown in FIG. 8, the injection position of the reactants may be higher than the inlet 10X. The injection position may be lower than the under surface of the flow-assisting blade 12 and may be higher than the lower surface. The types, positions, and number of injection materials can be appropriately selected.

Although a single reactor 10 may be used, plural reactors 10 may be disposed in series. Alternatively, plural reactors 10 may be disposed in parallel according to circumstances.

In these embodiments, any circulation system may be appropriately selected.

The shape of the flow-assisting blade according to the present invention can be appropriately selected, in addition to the disk shape. FIGS. 9 to 13 show other examples.

Figure 9:
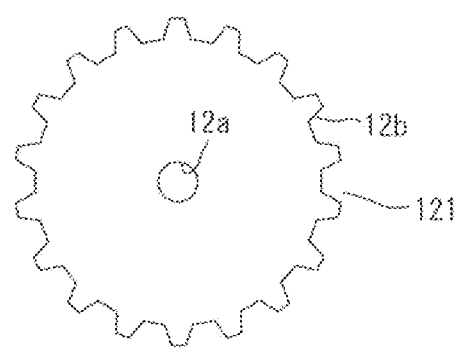
FIG. 9 is a schematic diagram illustrating a first example of the flow-assisting blade.

In the example shown in FIG. 9, a gear-shaped concave-convex portion 12b is formed in the periphery of a disk-shaped assisting blade 121. The concave-convex portion 12b increases the area in contact with a liquid to enhance the flowing effect. The reference sign 12a indicates the hole of engagement coupling with the rotary drive shaft.

Figure 10:
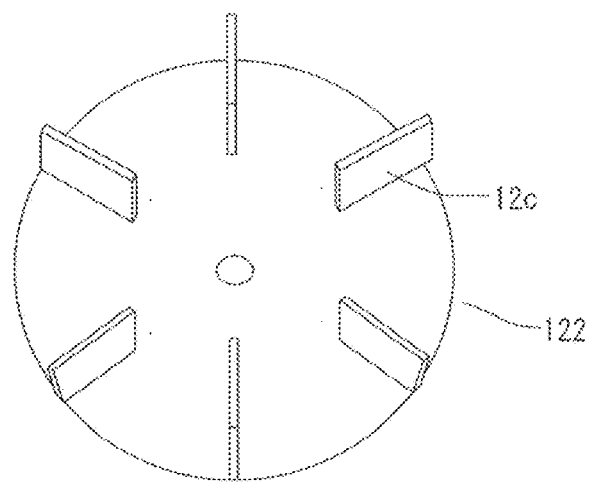
FIG. 10 is a schematic diagram illustrating a second example of the flow-assisting blade.

In the example shown in FIG. 10, plural straight blades 12c are disposed in the periphery of a disk-shaped assisting blade 122. The blades 12c cause a liquid scraping stirring effect to enhance the flowing effect.

Figure 11:
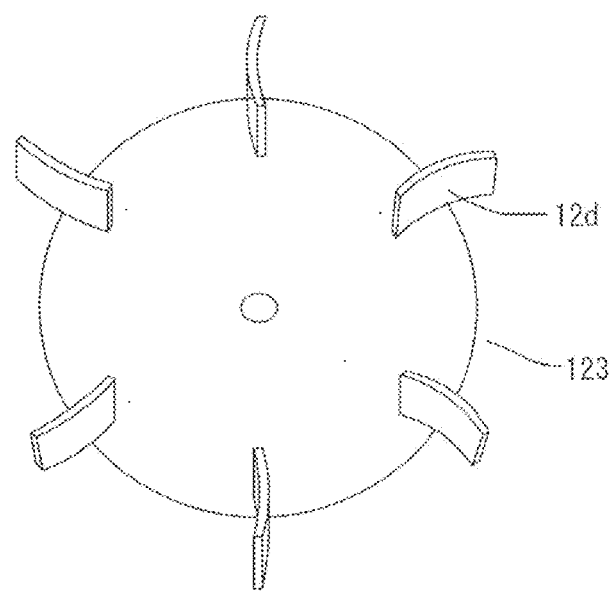
FIG. 11 is a schematic diagram illustrating a third example of the flow-assisting blade.

In the example shown in FIG. 11, a plurality of curved blades 12d is disposed in the periphery of a disk-shaped assisting blade 123. The blades 12d cause a liquid scraping stirring effect to enhance the flowing effect.

Figure 12:
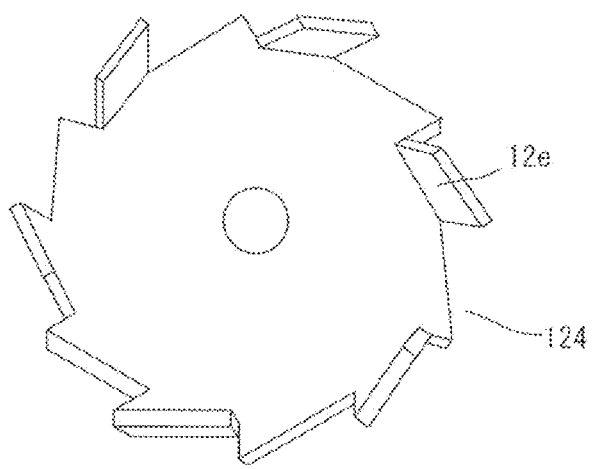
FIG. 12 is a schematic diagram illustrating a fourth example of the flow-assisting blade.

In the example shown in FIG. 12, sawtooth protrusions and plural oblique blades 12e are disposed in the periphery of a disk-shaped assisting blade 124. The blades 12e cause a liquid scraping stirring effect to enhance the flowing effect.

Figure 13:
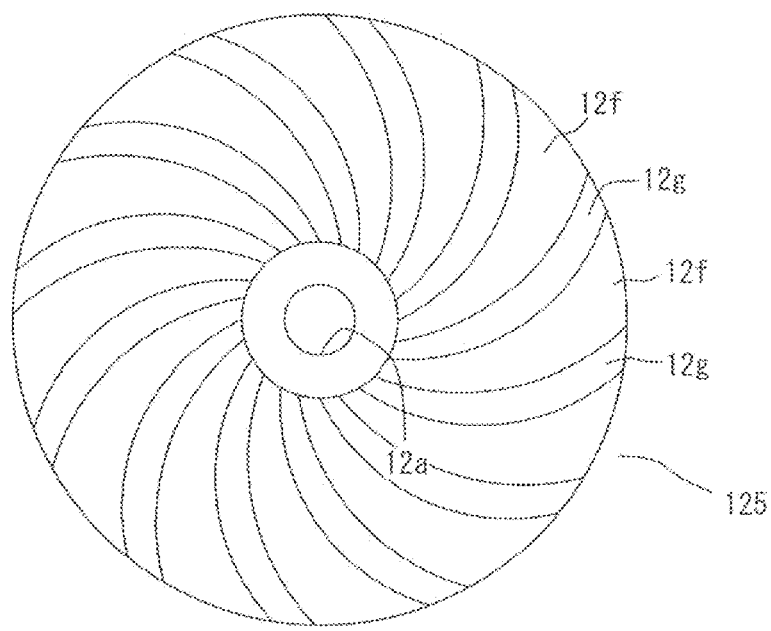
FIG. 13 is a schematic diagram illustrating a fifth example of the flow-assisting blade.

In the example shown in FIG. 13, a concave-convex portion composed of alternately formed involute curved protrusions 12f and recesses 12g is provided on the under surface of a disk-shaped assisting blade 125. The concave-convex portion causes a stirring effect to enhance the flowing effect.

Other examples of the flow-assisting blade include Fan Blades, Propeller Blades, Soft Cross Blades, Square Cross Blades, Butterfly Blades, Turbine Blades, and Helicopter Blades.

The ratio r/R of the radius r of the flow-assisting blade according to the present invention to the inner radius R of the reactor 10 is preferably ¼ to ¾.

The inflow rate Q [liter (L)/min] of a liquid into the reactor 10 is desirably 0.5 A to 10 A×60×10$^3$ [L/min] where the average flow rate is Vv [m/sec] and the cross-sectional area of the inlet 10X is A [m²]. The rotation speed of the flow-assisting blade is preferably ½ Vv or more, more preferably Vv or more in the tip speed.

Such a rotation speed of the assisting blade can cause necessarily and sufficiently strong circulation in a flow field formed by inflow of a liquid into the reactor 10 in the tangential direction and the randomly fluctuated vortex flow can be controlled stably along the tangential direction in the reactor 10 as shown by the observation photograph of FIG. 6. Consequently, the material liquid can be uniformly diffused in the flow field.

The flow-assisting blade exemplified above can accelerate the vortex flow without disordering the flow field.

Several embodiments other than the embodiment described above will be described.

Figure 14:
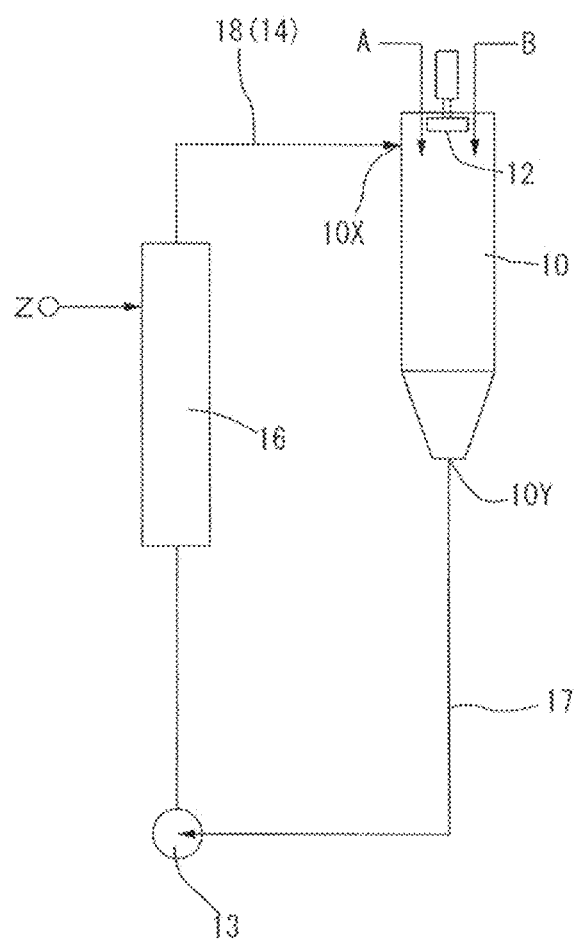
FIG. 14 is a schematic diagram according to another embodiment.

In the embodiment shown in FIG. 14, the regulator 16 performs not only control of the temperature but also addition of a material Z for pH adjustment, gas injection, or addition of a material to be contacted. In such a case, a diffusion-accelerating means, such as a stirring means, may be provided in the regulator 16. A regulator 16 having a large capacity may also be used as a container for retaining a liquid.

Figure 15:
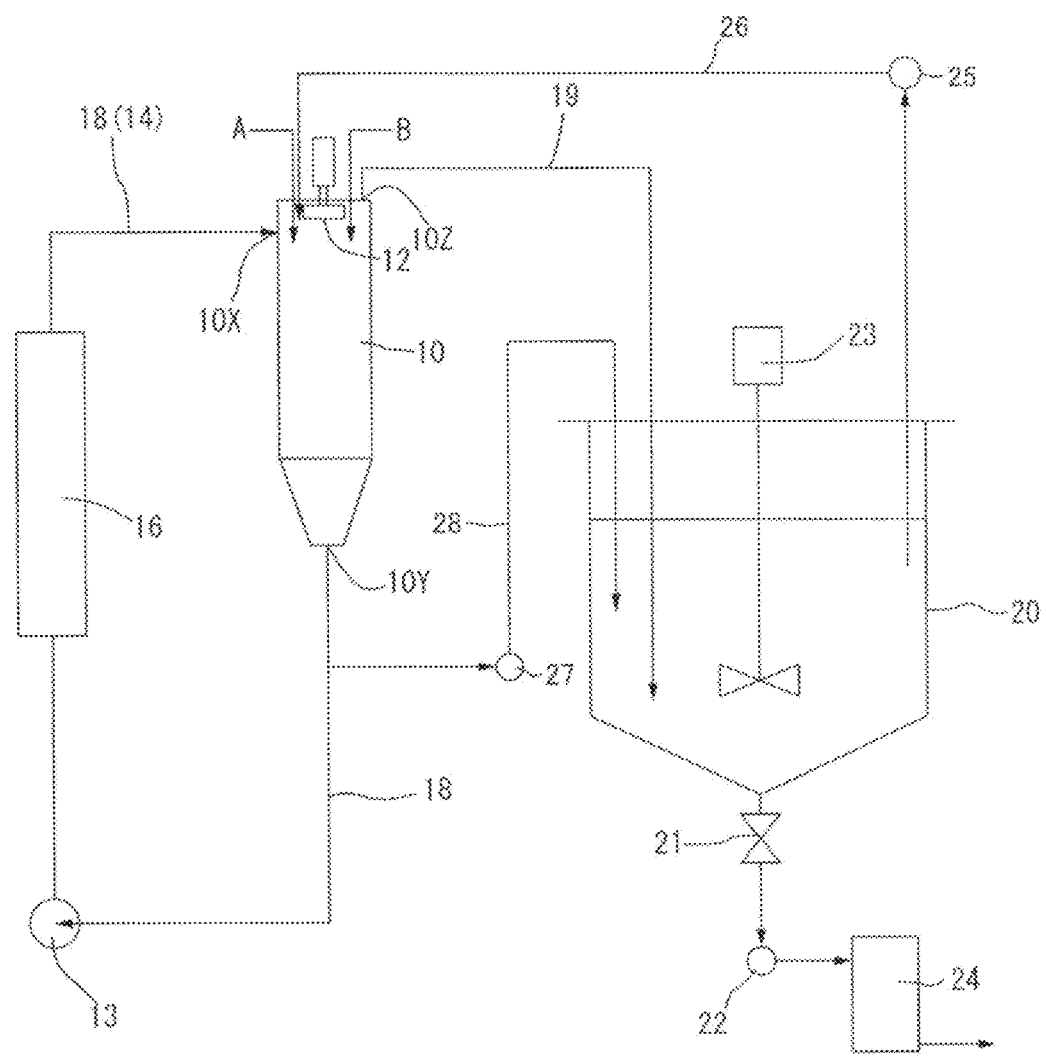
FIG. 15 is a schematic diagram according to another embodiment.

In the embodiment shown in FIG. 15, the liquid in the storage vessel 20 is partially sent back to the reactor 10 with a return pump 25 through a return path 26.

The contacted liquid discharged from the reactor 10 may be partially sent into the storage vessel 20 with a feed pump 27 through a feed path 28 as needed.

Figure 16:
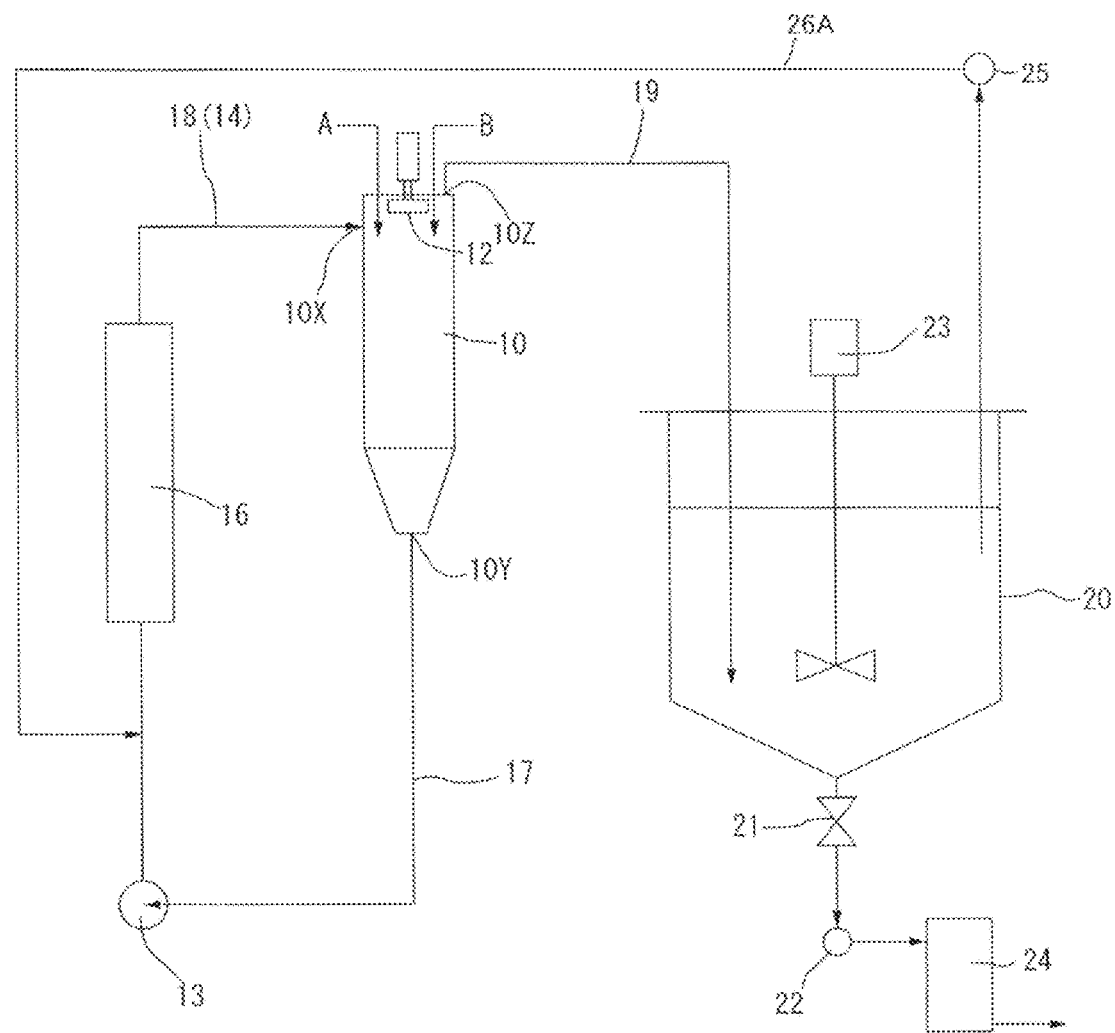
FIG. 16 is a schematic diagram according to another embodiment.
Figure 17:
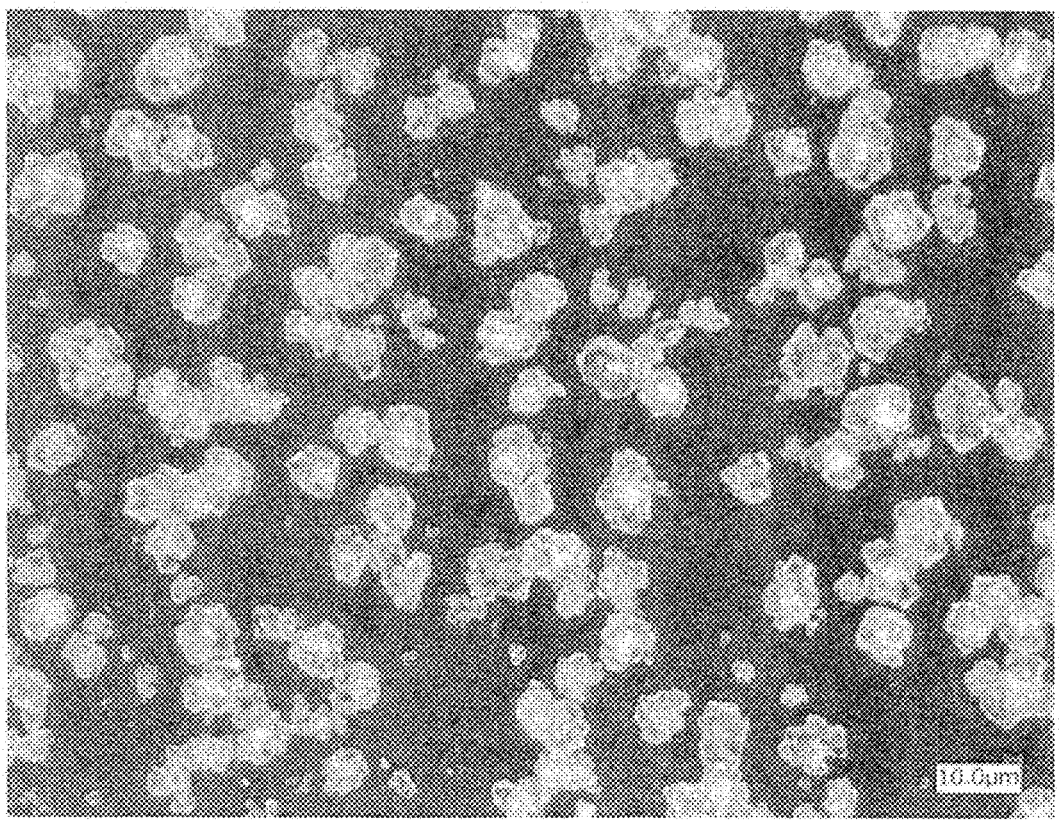
FIG. 17 is an optical photomicrograph of particles prepared in Example 1.
Figure 18:
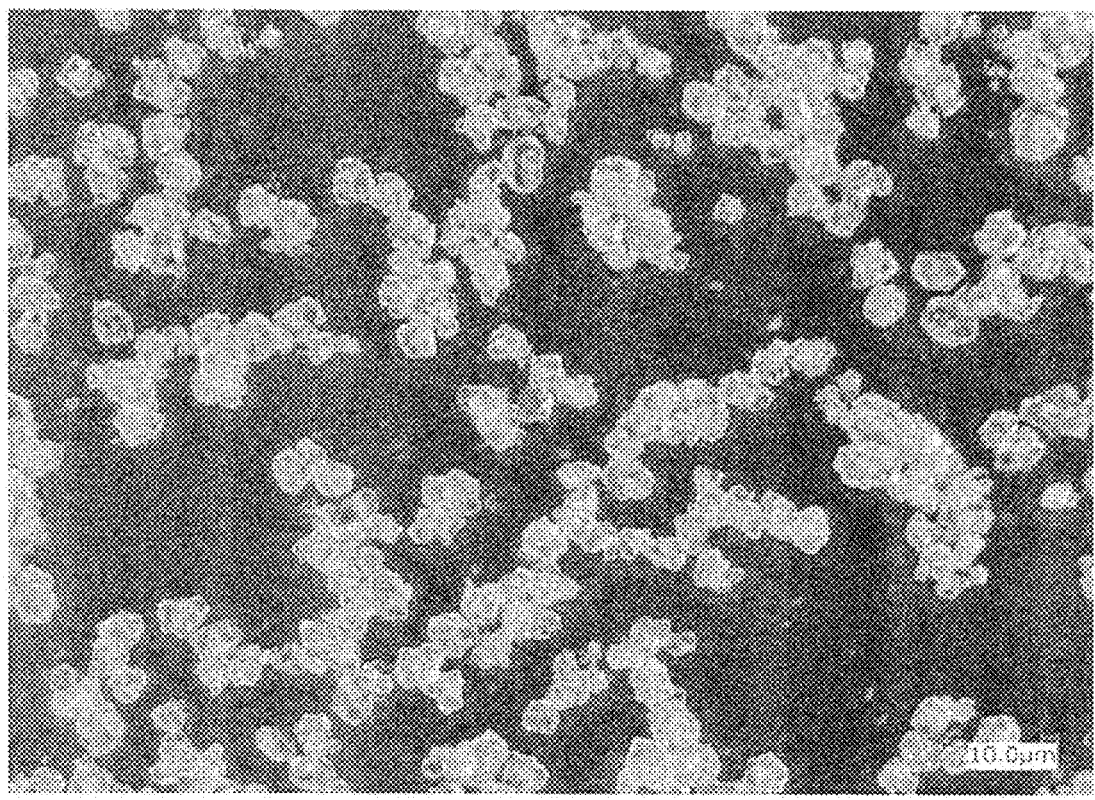
FIG. 18 is an optical photomicrograph of particles prepared in Comparative Example 1.
Figure 19:
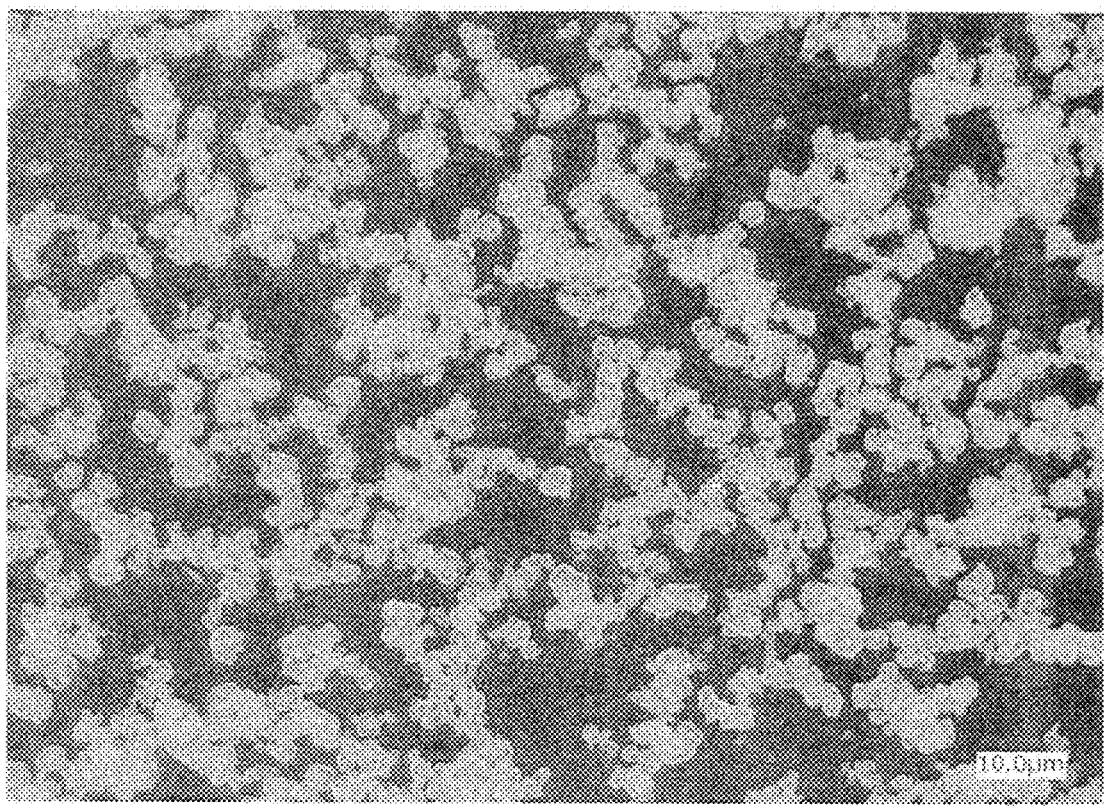
FIG. 19 is an optical photomicrograph of particles prepared in Example 2.
Figure 20:
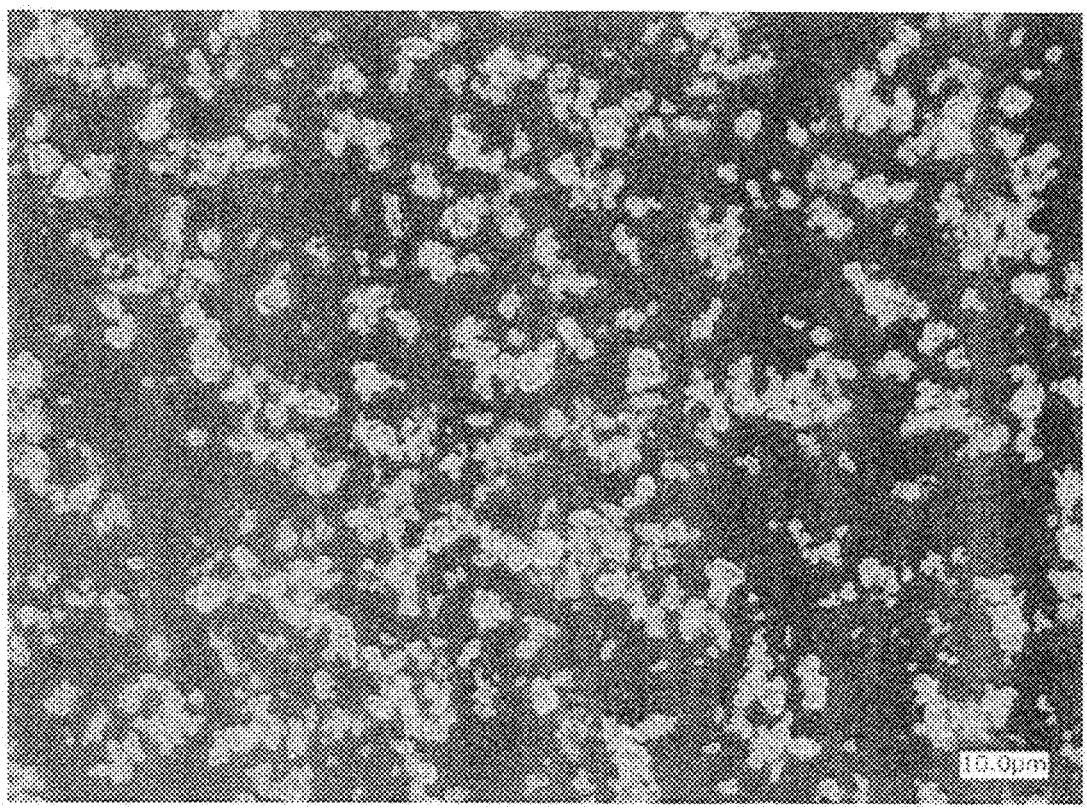
FIG. 20 is an optical photomicrograph of particles prepared in Comparative Example 2.

In the embodiment shown in FIG. 16, the liquid in the storage vessel 20 is partially sent back into the circulation system, for example, the inlet side of the regulator 16, with return pump 25 through a return path 26A.

The present invention can be applied to producing of particles, in particular, fine particles necessary in the industrial fields of cosmetics, catalysts, electronic materials, battery materials, fine ceramics, pharmaceuticals, and foods, as described above.

In particular, the present invention can be suitably applied to crystallization of two or more reactants, in addition to a poor solvent process.

Several examples will now be shown. The inventors have verified that the tendencies shown in the examples are similar for other materials.

EXAMPLES

Advantageous effects of the present invention will be clarified by the following examples and comparative examples.

(Production of Zinc Hydroxide)

In this example, zinc sulfate adjusted to 1 mol/L and 25% sodium hydroxide were injected into a reactor for the following reaction to produce zinc hydroxide:

$$ZnSO_4 + 2NaOH \rightarrow Zn(OH)_2 + Na_2SO_4$$

Table 1 shows the results of comparative evaluation after 180 minutes of an operation under conditions of 20° C., a pH of 12.5, an installed capacity of 5 L, and an average retention time of 30 min. The inlet diameter of the reactor was 13 mm.

The term "average retention time" is synonymous with the liquid injection time necessary for filling the operational capacity of the reactor and is that when zinc sulfate and sodium hydroxide were injected at 167 mL/min in total.

TABLE 1

| | Run No. | | | | | |
|---|---|---|---|---|---|---|
| | 1 Example 1 | 2 Comparative Example 1 | 3 Example 2 | 4 Comparative Example 2 | 5 Example 3 | 6 Comparative Example 3 |
| Target particles | $Zn(OH)_2$ | $Zn(OH)_2$ | $Zn(OH)_2$ | $Zn(OH)_2$ | $Al_2(OH)_3$ | $Al_2(OH)_3$ |
| Inflow rate L/min | 34 | 34 | 8 | 8 | 34 | 34 |
| Assisting blade tip speed m/sec | 4.3 | 0 | 4.3 | 0 | 4.3 | 0 |
| Average particle diameter μm | 17 | 13 | 38 | 30 | 2.5 | 3 |
| Evaluation of particle size distribution | 0.8 | 1.3 | 0.56 | 0.58 | 1.2 | 1.7 |

| | Run No. | | | | | |
|---|---|---|---|---|---|---|
| | 7 Example 4 | 8 Comparative Example 4 | 9 Example 5 | 10 Comparative Example 5 | 11 Example 6 | 12 Comparative Example 6 |
| Target particles | $Al_2(OH)_3$ | $Al_2(OH)_3$ | $H_2NCH_2$—COOH | $H_2NCH_2$—COOH | $CaCO_3$ | $CaCO_3$ |
| Inflow rate L/min | 15 | 15 | 24 | 24 | 34 | 34 |
| Assisting blade tip speed m/sec | 4.3 | 0 | 4.3 | 0 | 4.3 | 0 |
| Average particle diameter μm | 5 | 2 | 43.7 | 45 | 1.5 | 0.8 |
| Evaluation of particle size distribution | 1.2 | 1.0 | 1.9 | 2.6 | 1.2 | 1.6 |

(1) Low Inflow Rate (8 L/Min)

A sharp particle size distribution is obtained substantially regardless of presence or absence of an assisting blade.

The assisting blade can keep a sharp particle size distribution.

(2) High Inflow Rate (34 L/Min)

The presence of an assisting blade does not cause a substantial difference in the particle diameter but results in a sharp particle size distribution.

The particle size distribution was evaluated based on the accumulated value (D90–D10)/D50.

FIGS. 17 to 20 are optical photomicrographs of particles prepared in Example 1, Comparative Example 1, Example 2, and Comparative Example 2.

(Production of Aluminum Hydroxide)

Aluminum hydroxide was prepared under the same conditions, and the effects by installation of a flow-assisting blade were investigated. Table 1 shows the results.

Table 1 demonstrates that the particle size distribution in Example 3 in which a flow-assisting blade was installed was sharper than that in Comparative Example 3 in which the flow-assisting blade was not installed, although no substantial difference was observed in the particle diameter.

In Example 4 and Comparative Example 4 at a low inflow rate under the same conditions, the particle size in Example 4 was larger than that in Comparative Example 4. In Example 4, aggregation of particles was accelerated by the effect of assisting the growth of agglomerated particles.

(Production of Glycine)

A saturated glycine liquid [(20 g+α)/100 g] at 20° C. was used as a starting mother liquor and was circulated at 34 L/min. A 99.5% ethanol liquid was injected into the reactor to recrystallize glycine. The volume of the starting mother liquor was 2 L, and the ethanol liquid was injected into the reactor at 1.5 L/min for 80 seconds. The experiment was terminated at the time when the liquid volume in the device reached 4 L.

Figure 21:
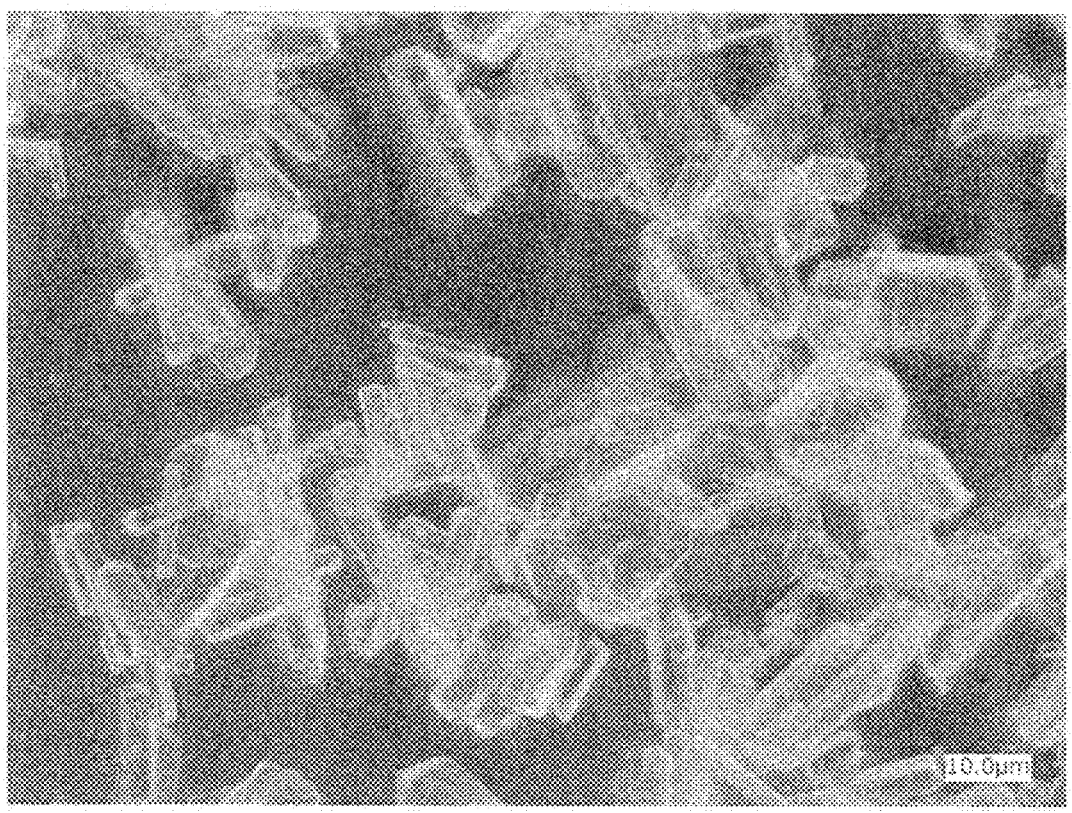
FIG. 21 is an optical photomicrograph of particles prepared in Example 5.
Figure 22:
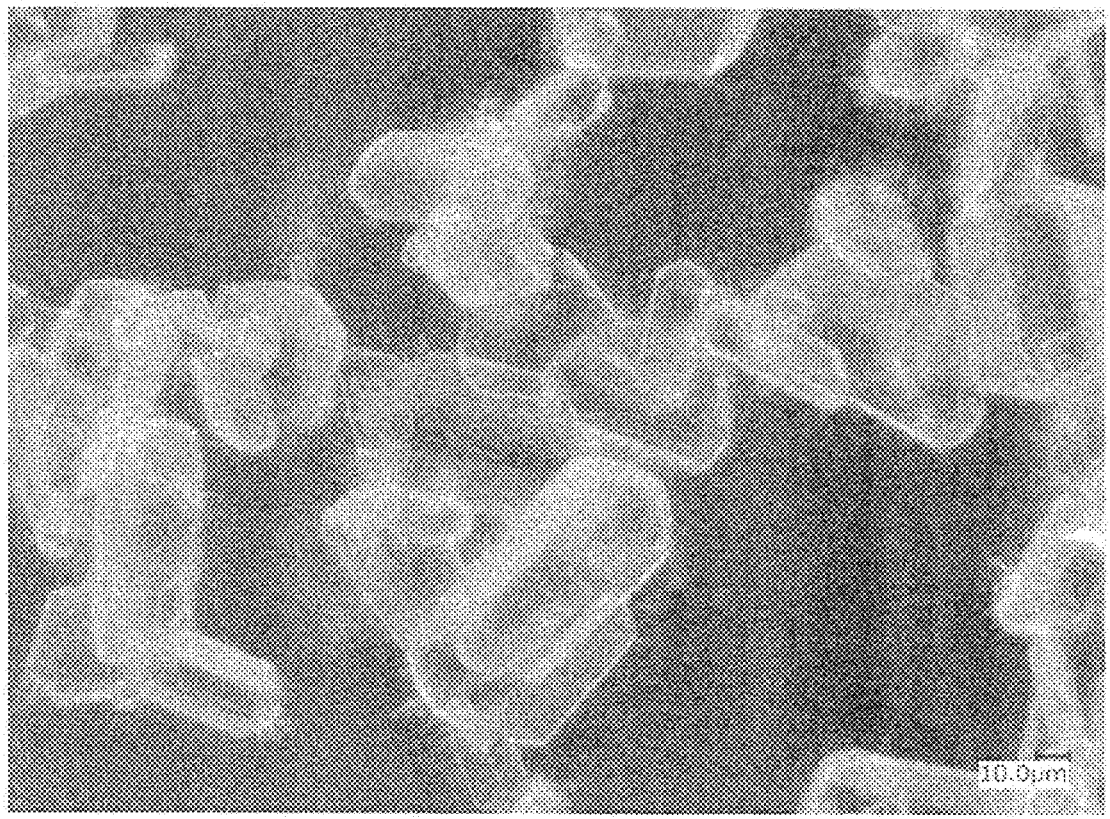
FIG. 22 is an optical photomicrograph of particles prepared in Comparative Example 5.

The results are shown in Table 1. FIGS. 21 and 22 are optical photomicrographs of the particles prepared in Example 5 and Comparative Example 5.

Table 1 demonstrates that the particle size distribution in Example 5 in which a flow-assisting blade was installed was sharper than that in Comparative Example 5 in which the flow-assisting blade was not installed. It was also demonstrated that the aspect ratios of the particles in FIG. 21 (Example 5) are almost constant, whereas the aspect ratios of the particles in FIG. 22 (Example 5) are somewhat irregular.

(Production of Calcium Carbonate)

A 10 wt % calcium hydroxide liquid (3 L) at 20° C. was used as a starting mother liquor and was circulated at 34 L/min. $CO_2$ gas was injected into the reactor at 600 mL/min, and the experiment was terminated at the time when the pH reached 7 or less.

Figure 23:
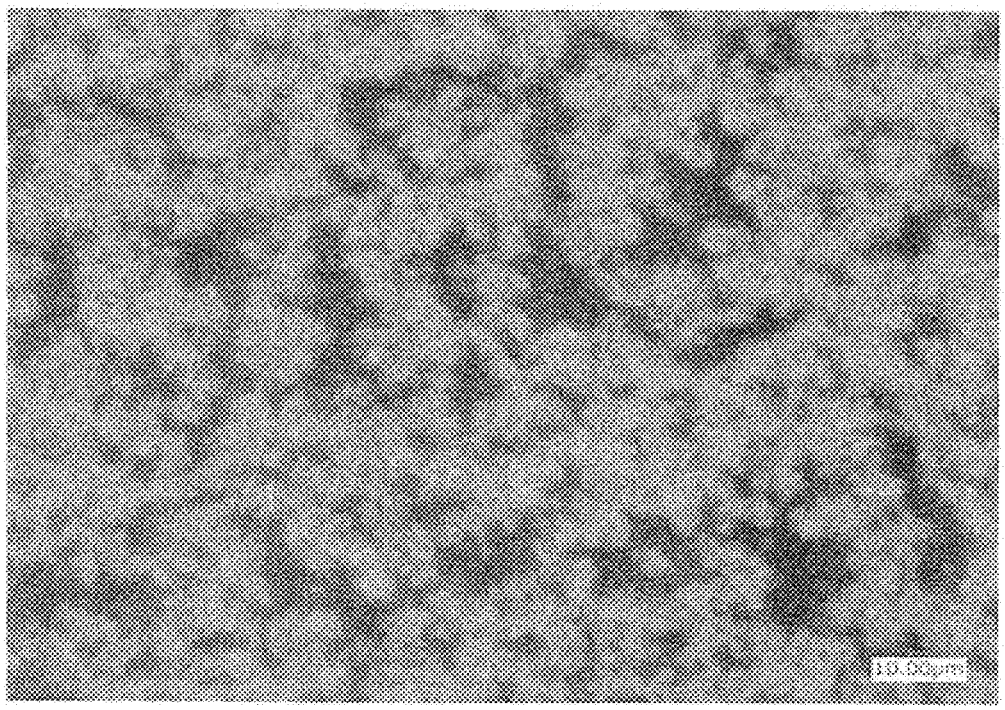
FIG. 23 is an optical photomicrograph of particles prepared in Example 6.
Figure 24:
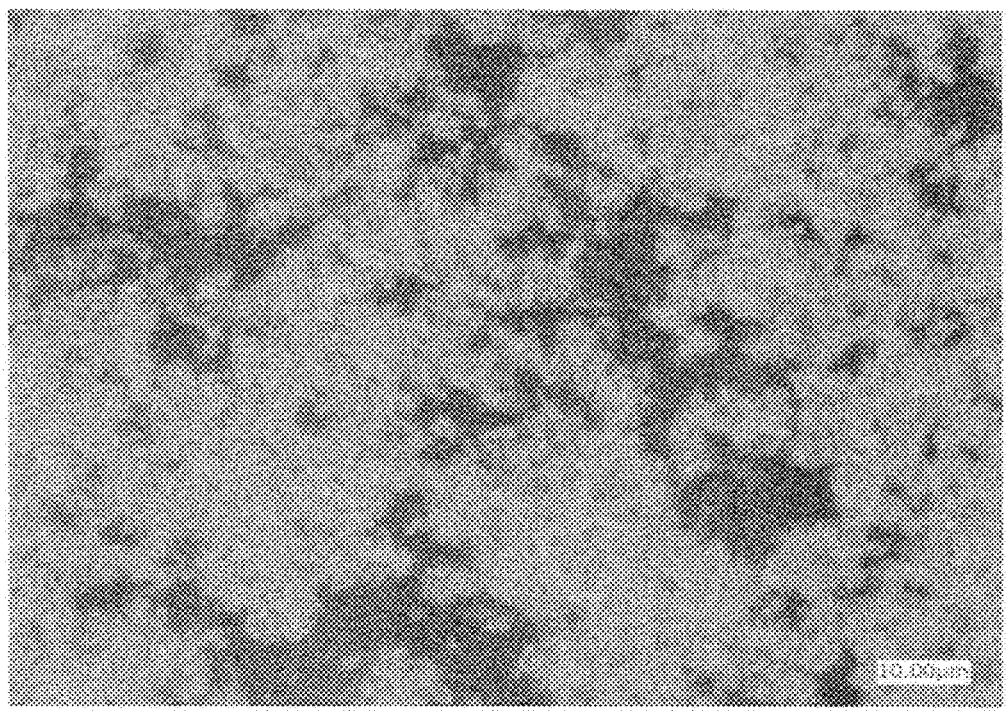
FIG. 24 is an optical photomicrograph of particles prepared in Comparative Example 6.
Figure 25:
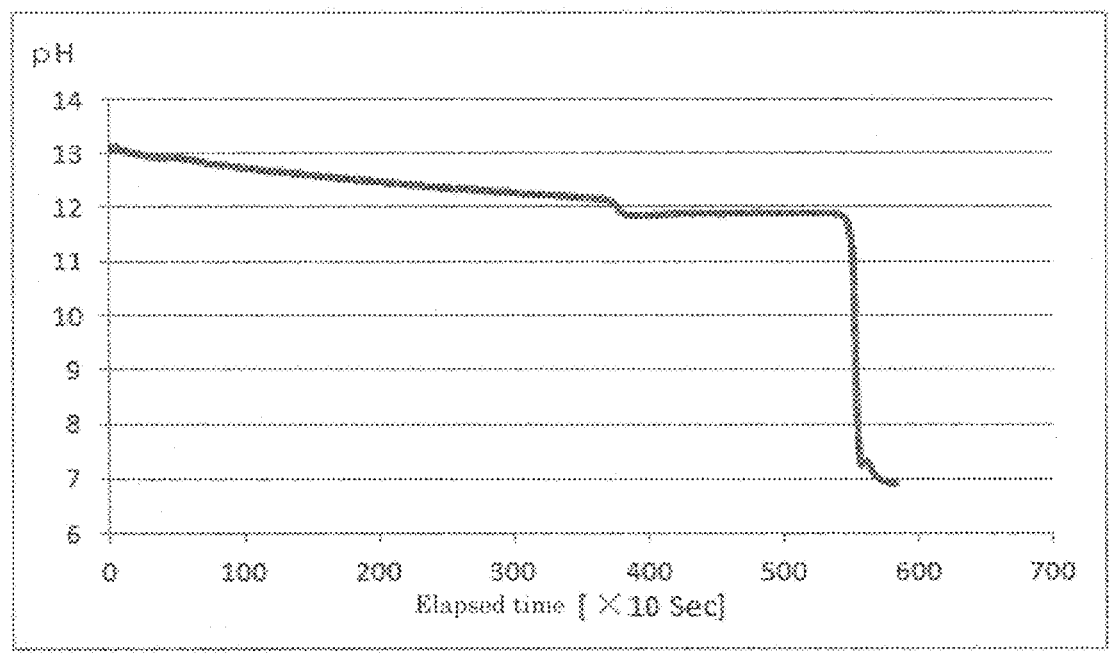
FIG. 25 is a pH curve in Example 6.
Figure 26:
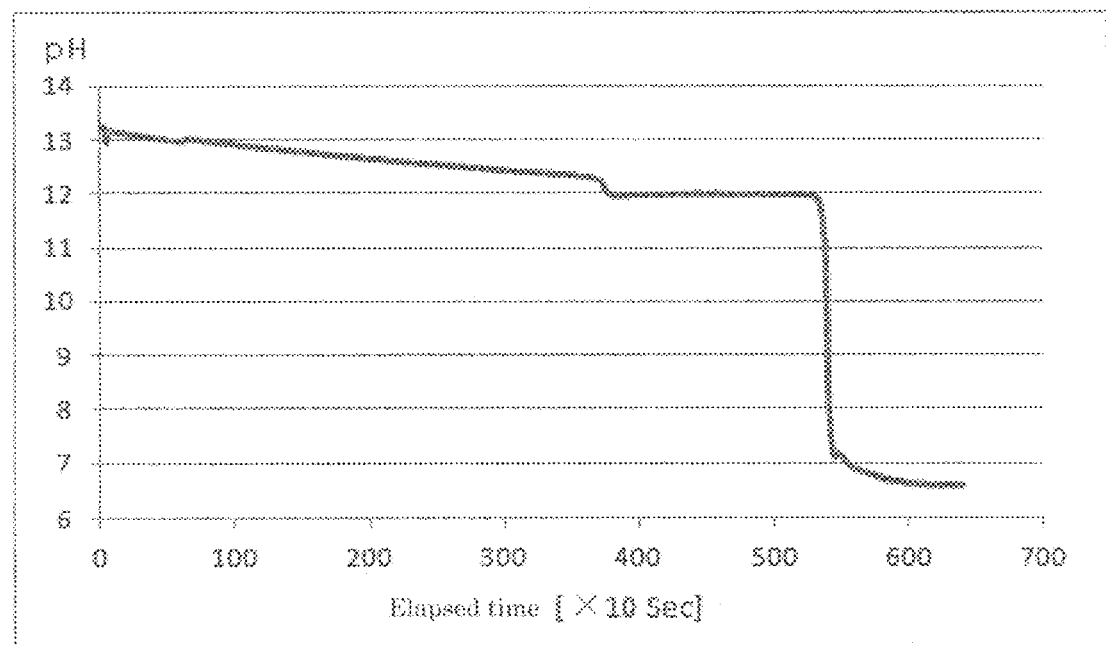
FIG. 26 is a pH curve in Comparative Example 6.

The results are shown in Table 1. FIGS. 23 and 24 are optical photomicrographs of the particles prepared in Example 6 and Comparative Example 6. FIGS. 25 and 26 show the pH curved obtained in Example 6 and Comparative Example 6.

In Comparative Example 7, a stirred reactor equipped with a two-stage stirring blade and a draft tube was used. A 10 wt % calcium hydroxide liquid (3 L) at 20° C. was used as a starting mother liquor, and $CO_2$ gas was injected in the vicinity of the stirring blade to perform stirring with the $CO_2$ gas and reaction with calcium hydroxide, and the experiment was terminated at the time when the pH reached 7 or less.

Figure 27:
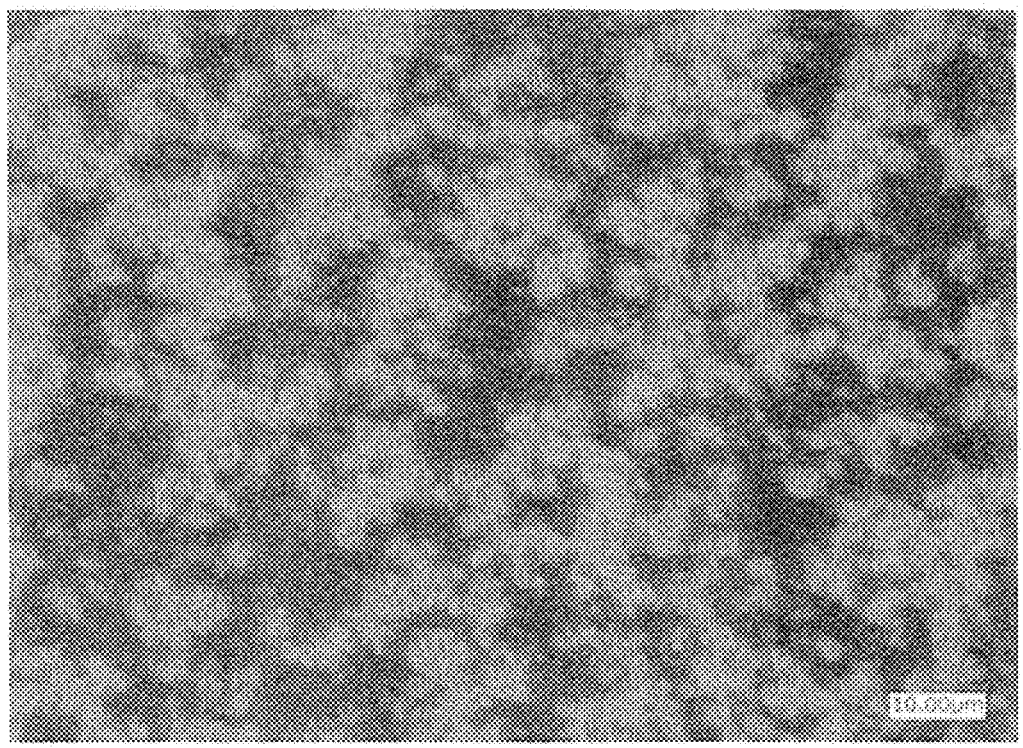
FIG. 27 is an optical photomicrograph of particles prepared in Comparative Example 7.
Figure 28:
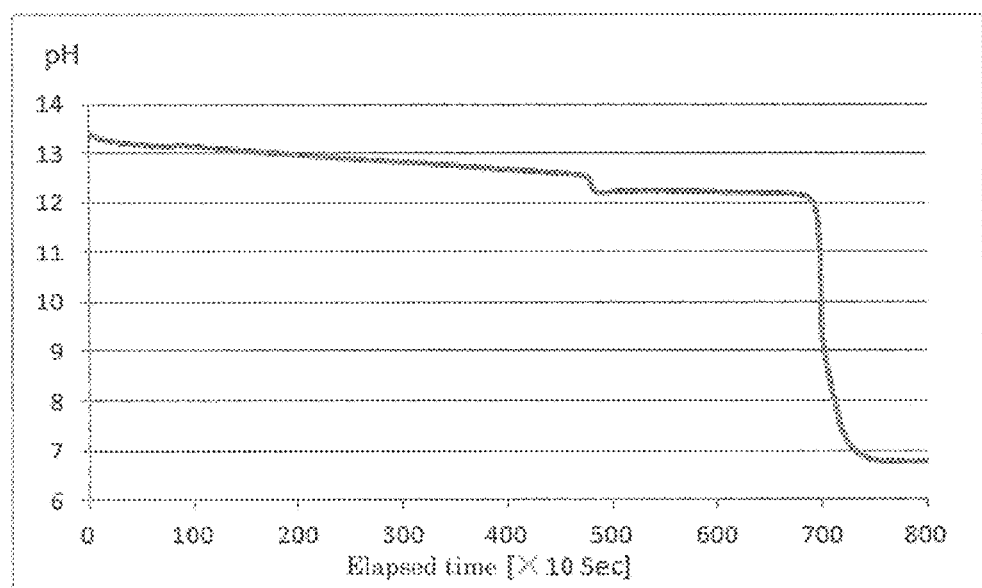
FIG. 28 is a pH curve in Comparative Example 7.

The results are shown in Table 2. FIG. 27 is an optical photomicrograph of the particles prepared in Comparative Example 7. FIG. 28 shows a pH curve obtained in Comparative Example 7.

TABLE 2

| | Run No. 13 Comparative Example 7 |
|---|---|
| Target particles | $CaCO_3$ |
| Rotation speed of stirring blade r.p.m | 1000 |
| Stirring blade tip speed m/sec | 2.1 |
| Average particle diameter μm | 2 |
| Evaluation of particle size distribution | 1.6 |

Tables 1 and 2 demonstrate that Example 6, provided with a flow-assisting blade, accelerated aggregation of particles by the effect of assisting and an increase in the diameter of agglomerated particles compared to Comparative Example 6, and prepared particles with a sharp particle size distribution compared to those in Comparative Examples 6 and 7. Comparison of the pH curves of Example 6 and Comparative Example 6 demonstrates no substantial difference in the time required for the reaction. Example 6 demonstrates that the time required for the reaction was considerably shortened compared with Comparative Example 7.

REFERENCE SIGNS LIST 10 reactor
10X inlet
10Y outlet
10Z overflow port
12 flow-assisting blade
14 liquid
15A, 15B injection nozzle
16 regulator
17, 18 circulation path
A, B reactant

The invention claimed is:
1. A method of producing particles by bringing plural dissimilar materials into contact with each other, the method comprising:
feeding a liquid into a reactor from a first end portion of the reactor such that the liquid flows along an inner peripheral surface of the reactor and generating a vortex flow toward a second end portion in the reactor by the feeding of the liquid;
disposing a flow-assisting blade capable of rotating around a central axis line of the reactor and rotating the flow-assisting blade; and
injecting materials to be contacted into the reactor, discharging a contacted liquid from the second end portion of the reactor, and generating particles in the contacted liquid;
wherein the flow-assisting blade has a radius r and wherein the reactor has an inner radius R, and wherein a ratio r/R of the radius r of the flow-assisting blade to the inner radius R of the reactor is ¼ to ¾;
wherein an inlet for the liquid into the reactor has a cross-sectional area of A, and the liquid has an inflow rate Q into the reactor of 0.5 A to 10 A×60×$10^3$; and
wherein an average flow rate of the liquid at the inlet is Vv, and the flow-assisting blade is rotated at a speed that is ½ Vv or more.
2. The method of producing particles according to claim 1, wherein all or part of the contacted liquid discharged from the second end portion of the reactor is fed into the reactor from the first end portion of the reactor such that the liquid flows along the inner peripheral surface of the reactor.

3. The method of producing particles according to claim 2, wherein part of the contacted liquid is extracted from a circulation system that transfers the contacted liquid discharged from the second end portion of the reactor to the first end portion of the reactor, and the particles are recovered by solid-liquid separation.

4. The method of producing particles according to claim 1, wherein the liquid is fed into the reactor from the first end portion at an inflow velocity of 0.5 m/sec or more.

5. The method of producing particles according to claim 1, wherein the reactor has a ratio L/D of 2 or more of the longitudinal length L to the diameter D of an internal space of the reactor.

6. The method of producing particles according to claim 1, wherein the flow-assisting blade has a disk shape intersecting with the central axis line of the reactor.

7. The method of producing particles according to claim 1, wherein the flow-assisting blade has a disk shape having a concave-convex portion in a periphery thereof.

8. The method of producing particles according to claim 1, wherein the flow-assisting blade has a disk-shaped body intersecting the central axis line of the reactor and a protrusion protruding to the second side at least in a periphery of the disk-shaped body and intersecting a circle having a center on the central axis line.

9. The method of producing particles according to claim 1, wherein the flow-assisting blade is located closer to the first end portion of the reactor than where the liquid is fed in the first end portion of the reactor.

10. The method of producing particles according to claim 1, wherein a position at which the materials to be contacted is injected, is disposed outboard from the flow-assisting blade in the direction of the radius around the central axis line in the reactor.

* * * * *